US00PP10777P

United States Patent [19]

Wain

[11] Patent Number: Plant 10,777

[45] Date of Patent: Feb. 2, 1999

[54] CHRYSANTHEMUM PLANT NAMED 'LUCKY TIME'

[75] Inventor: Peter Wain, Hapshire, United Kingdom

[73] Assignee: Cleangro, Ltd., West Sussex, England

[21] Appl. No.: 838,357

[22] Filed: Apr. 8, 1997

[51] Int. Cl.[6] ..... A01H 5/00

[52] U.S. Cl. ..... Plt./82.4

[58] Field of Search ..... Plt./74.1, 82.1, Plt./82.4

[56] References Cited

U.S. PATENT DOCUMENTS

P.P. 8,216 4/1993 Van der Knaap ..... Plt./74.1

P.P. 8,245 6/1993 Van der Knaap ..... Plt./82.1

OTHER PUBLICATIONS

UPOU–ROM, 1997 Mar., Plant Variety Databsase, GTI Jouve Retrieval Software, Citation for 'Lucky Time'.

*Primary Examiner*—Howard J. Locker

*Attorney, Agent, or Firm*—Christie, Parker & Hale, LLP

[57] ABSTRACT

A new and distinct variety of Chrysanthemum plant having light pink flowers with purple centers. Ray floret color fades to white as the bloom ages.

2 Drawing Sheets

BACKGROUND OF THE INVENTION

The present invention is directed to a new and distinct variety of Chrysanthemum botanically classified as *Dendranthema grandiflora*. The varietal denomination of the new Chrysanthemum is 'Lucky Time'.

The female and male parents of the new variety are undistributed, unpatented seedlings identified as 'P22-13 and 'P45-19, respectively. The new variety has been asexually reproduced by vegetative cuttings in Ventura County, Calif. and the distinguishing characteristics are retained through successive generations of asexual reproduction.

SUMMARY OF THE INVENTION

'Lucky Time' is a spray type pot forcing chrysanthemum plant variety producing flowers with light pink ray florets and purple centers on a plant capable of being grown commercially in a greenhouse. Ray floret color fades to white with increasing age of the bloom.

BRIEF DESCRIPTION OF ILLUSTRATIONS

The accompanying photographs show typical specimens of the new variety with colors being as nearly true as possible with illustrations of this type. One illustration shows 'Lucky Time' grown as a pinched spray pot mum and the other illustration is a close-up of the flowers.

DESCRIPTION OF THE PLANT

The following description of the new variety is of specimens grown in a greenhouse in Oxnard, Ventura County, Calif. in the month of October. 'Lucky Time' has not been observed under all possible environmental conditions. The phenotype may vary significantly with variations in the environment such as temperature, light intensity, day length and cultural conditions. Color values are taken from The Royal Horticultural Society Colour Chart.

Plants of the new variety have been grown successfully under temperature conditions averaging about 65° F. at night and about 75–85° F. during the day under light conditions of about 5,000–6,000 Foot candles. The plants respond well to use of growth retardant, such as a treatment with growth regulator B9 at about 2000 ppm. To produce a commercial product the plants may be pinched once. It has been observed that the shelf life of 'Lucky Time' is about 24 days with the response time of about 8.5 weeks.

Plant

Habit: Upright and branching.

Height: About 26 cm after one application of growth regulator B9 as described.

Branching characteristics: Very good brancher both in quality and quantity.

Number of breaks from pinch: About 3 to 4.

Typical container size to be grown in: 4", 5", 6", 8", 10".

Length of lateral branches:

*Average.*—About 18 cm.

Stem color: Near 143C.

Foliage

Leaf arrangement: Alternate.

Number of leaves per lateral Branch:

*Average.*—About 8 .

(1) *Size.*—Length—Average about 8.25cm; Width—Average about 4.2cm.

(2) *Shape.*—Ovate.

(3) *Attachment.*—Petioled.

(4) *Apex.*—Acute (some obtuse).

(5) *Base.*—Tapered.

| (6) Color: | Mature | Young |
|---|---|---|
| Top: | Near 137A | Near 137B |
| Bottom: | Near 137C | Near 137C |

Margin: Lobed with slight serrations.

Aspect: Flat, curling under with age.

Surface characteristics:

*Top—puberulent.*

*Bottom—puberulent.*

Venation: Palmately net; main veins prominent on underside of leaf; main vein coloration is near 143D; veinlet coloration is near 137D.

Petiole:
(1) *Length.*—About 2.25 cm.
(2) *Color.*—Near 143C.
(3) *Other Characteristics.*—Winged, tomentose.
Stipule: Occasionally present, 2, 1 to 3 lobed.

Flower

Inflorescence form: Cymose cluster.
*Flower form.*—Anemone.
*Flower shape.*—Irregular circle.
*Flower color (general).*—Light pink (fading to white as the bloom ages) with purple centers.
Blooms: Average about 6 blooms per branch.
(1) *Diameter.*—About 5 cm.
(2) *Depth.*—About 1.5 cm.
(3) *Longevity on plant.*—About 24 days.
Sepal:
(1) *Number.*—About 25.
(2) *Color.*—Near 137A.
(3) *General appearance.*—Highly membranous.
Peduncle:
(1) *Length.*—Average about 5 cm.
(2) *Habit.*—Upright, very slight curve.
(3) *Surface.*—Tomentose.
(4) *Color.*—Near 138B.
(5) *Strength.*—Weak.
Bud:
(1) *Shape.*—Flattened sphere.
(2) *Diameter.*—Avg. about 0.9 cm.
(3) *Color.*—Near 144A.
(4) *Height.*—About 0.4 cm.
Ray florets:
(1) *Number per flower.*—About 30.
(2) *Texture.*—Matte.
(3) *Shape.*—Elliptic.
(4) *Apex.*—3 small lobes.
(5) *Base.*—Tapered.
(6) *Margin.*—Entire.
(7) *Aspect.*—Curled back.
(8) *Length.*—Avg. About 2.5 cm.
(9) *Width.*—Avg. About 0.4 cm.
*Color floret.*—Upper side: Immature: Near 62D. Mature: Near 155C. Fading: Near 155D. Under side: Immature: Near 62D. Mature: Near 155D. Fading: Near 155D.
Disc florets:
(1) *Number per flower.*—Average about 210.
(2) *Texture.*—Matte.
(3) *Shape.*—Tubular, flattened.
(4) *Apex.*—5 lobed with acute tips, 2 cut more deeply
(5) *Length.*—Average about 1.5 cm
(6) *Width.*—Average about 0.3 cm
(7) *Fragrance.*—Light, sweet, musty
*Color.*—59C. Immature: Near 59C. Mature: Near 59D. Fading: Near 65A.
Description of flower as it ages: Ray florets become very dry and shrivel before disc florets are spent. Eye stays dark and disc florets remain tightly held.

Reproductive Organs

Ray florets:
*Pistillate.*—(1) Pistil number: 1 per floret. (2) Ovary shape: Domed sphere. (3) Stigma shape: Forked, angled outward. (4) Stigma color: Near 12A. (5) Style length: About 0.3 cm. (6) Style color: Near 2D.
Disc florets:
*Pistillate.*—Pistil number: 1 per floret. (2) Stigma shape: Forked out, near 7A. (3) Style length: About 0.3 cm, near 154D.
*Staminate.*—(1) Stamen Number: 5.

What is claimed is:

1. A new and distinct variety of Chrysanthemum plant substantially as herein shown and described.

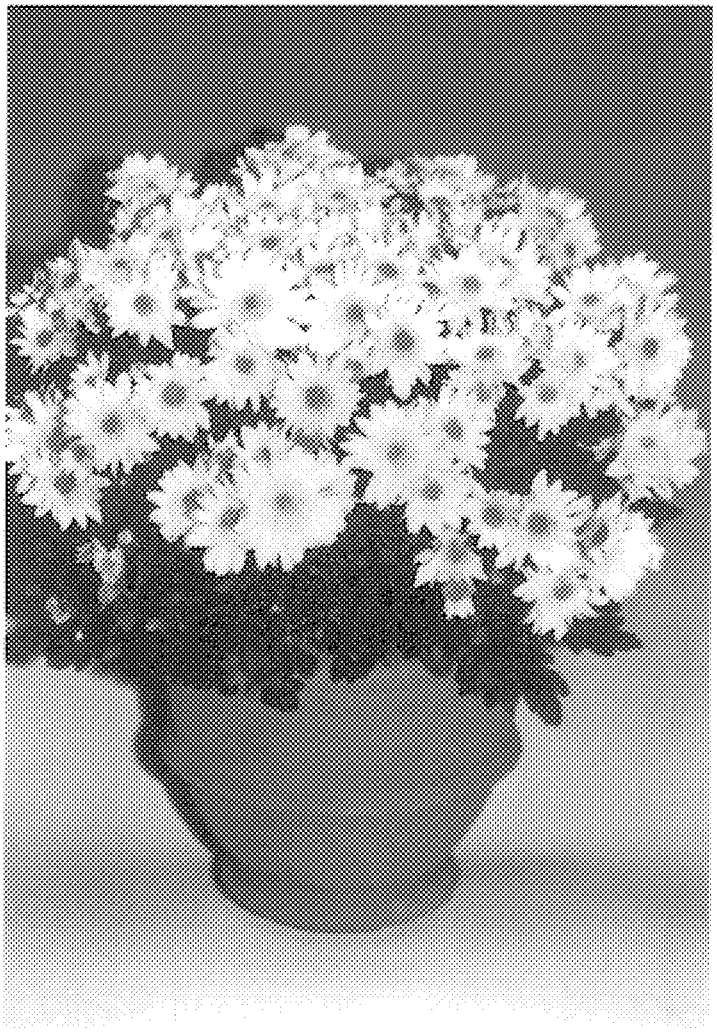

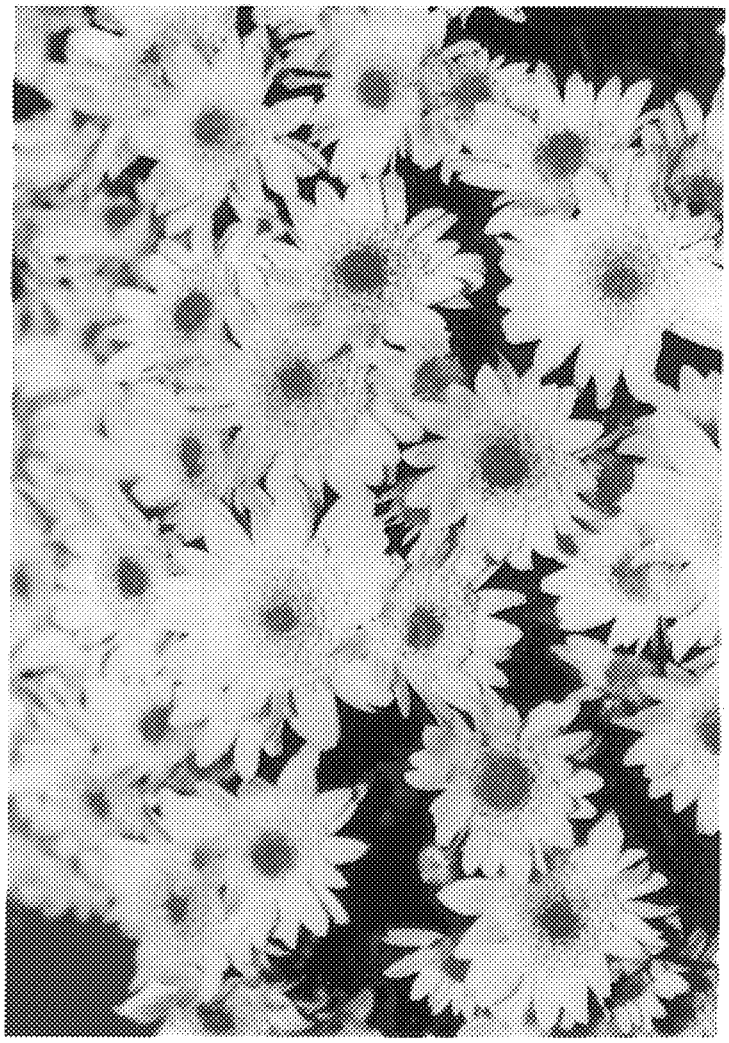

* * * * *